United States Patent [19]
Grande et al.

[11] Patent Number: 6,068,478
[45] Date of Patent: May 30, 2000

[54] IMPRESSION SYSTEM FOR AN END OF AN IMPLANT PROJECTING FROM A HUMAN TISSUE STRUCTURE

[75] Inventors: Vincenzo Grande, Möhlin; Reto Baumgartner, Frenkendorf; Roger Tschirky, Ettingen, all of Switzerland

[73] Assignee: Institut Straumann AG, Waldenburg, Switzerland

[21] Appl. No.: 09/066,321

[22] PCT Filed: Jan. 31, 1997

[86] PCT No.: PCT/CH97/00031

§ 371 Date: Apr. 28, 1998

§ 102(e) Date: Apr. 28, 1998

[87] PCT Pub. No.: WO97/28755

PCT Pub. Date: Aug. 14, 1997

[30] Foreign Application Priority Data

Feb. 8, 1996 [CH] Switzerland ................................ 326/96

[51] Int. Cl.[7] ................................................. A61C 8/00
[52] U.S. Cl. ............................................. 433/172; 433/173
[58] Field of Search ................................. 433/172, 173, 433/174

[56] References Cited

FOREIGN PATENT DOCUMENTS 4415670  9/1995  Germany .

OTHER PUBLICATIONS

Orale Implantologie, 2 ed., Georg Thieme Verlag, Stuttgart, New York, 1994, pp. 202–209.

Oral Implantology, 2d rev. ed., Georg Thieme, Verlag, Stuttgart, New York, 1996, pp. 198–204.

Primary Examiner—John J. Wilson
Attorney, Agent, or Firm—Selitto & Associates

[57] ABSTRACT

An impression system includes an impression cap (4) for transferring an end, protruding from a human tissue structure, of an implant (1) which is fitted in the human body, including possible superstructures, to a master cast. The outwardly directed implant end has an undercut contour on its outside, and the impression cap (4) has a geometry which complements the undercut contour and engages therein. The undercut contour is formed either by an implant geometry tapering in a trumpet shape towards the implant bed, or by a recess near the implant end. Taking an impression and producing a master cast are greatly simplified with the impression system. In addition, the actual geometrical situation on the patient can be transferred to the master cast with greater precision.

42 Claims, 10 Drawing Sheets

IMPRESSION SYSTEM FOR AN END OF AN IMPLANT PROJECTING FROM A HUMAN TISSUE STRUCTURE

FIELD

The present invention relates to an impression system with an impression cap for an implant fitted in the human body in order to transfer the implant end protruding from the tissue structure, including possible superstructures on this implant end, to a master cast.

PRIOR ART

The following discussion refers in the first instance to the example of dental implants. For taking an impression of the situation in the patient's mouth and for transferring the impression obtained to a master cast, on which the tooth replacement is then modelled, a number of elements have hitherto been used. The work steps that have had to be performed to date, and the elements used in these work steps, are dealt with in detail by SCHROEDER, A.; SUTTER, F.; BUSER, D.; KREKELER, G.: Orale Implantologie [Oral implantology], Georg Thieme Verlag Stuttgart, 2nd edition, 1994, page 202 et seq. On the one hand, the assembling of the elements in the patient's mouth, particularly in the area of the molars, is problematic because of the resulting overall height of the elements, especially if a screwing instrument has to be used as well. Moreover, the work procedures are demanding for the patient, and they are time-consuming as regards impression-taking and production of the master cast. In addition to this, inaccuracies occur. The difficulties result primarily from the fact that the impression cap does not hold itself on the implant fitted in the mouth or on the manipulation implant to be used subsequently in the production of the master cast. DE 44 15 670 A1 discloses an impression cap which, at the open end facing the implant, has resilient flaps which, when applied, engage over the shoulder of the conical superstructure, the latter being fitted into the implant. The impression cap described there cannot therefore be used for taking an impression of the implant end protruding from the gingiva and projecting into the mouth, but instead only for taking an impression of the outer contour of the superstructure while the implant is positioned below the gingiva.

OBJECT OF THE INVENTION

In view of the hitherto costly and in some cases inaccurate impression-taking and production of the master cast, and in view of the fact that the impression caps can only be used conditionally, the invention is based on the problem of creating an impression system with an impression cap which is suitable for transferring, to a master cast, an implant end, on which a superstructure can be located, protruding from the human tissue structure. Here, the impression cap, embedded in the impression compound present in the impression tray, must be able to be removed from the fitted implant, and it must be able to receive the manipulation implant equally securely. It must be possible for the impression cap to be used for the most varied types of implants, even when very different abutments are fitted therein, for example abutments which are straight or angled, conical or with a polygonal head, solid or with an internal thread.

SUMMARY

The impression system comprises as its principal component an impression cap for transferring an end, protruding from a human tissue structure, of an implant which is fitted in the human body, including possible superstructures, to a master cast. The outwardly directed implant end has an undercut contour on its outside, and the impression cap has a geometry which complements the undercut contour and engages therein. The undercut contour is formed either by an implant geometry tapering in a trumpet shape towards the implant bed, or by a recess near the implant end.

The engaging geometry provided on the impression cap is advantageously a snap element in the form of a circular lip, or it is formed by individual gripping members. In a preferred embodiment, the implant end is trumpet-shaped, and it has an angled shoulder portion in the form of an implant shoulder in the area of greatest diameter. The cap shoulder provided on the impression cap is supported at least partially on the implant shoulder.

On the outer circumference, the impression cap can have retention plates generated by radial grooving and/or radially directed apertures. The impression cap is closed on one side, or it has an axial channel passage. Either the channel passage of the impression cap remains free, or the abutment of a superstructure and/or a slide sleeve can be fitted therein. The slide sleeve has an inner contour complementing the abutment, and at least the lower edge of the sleeve section of the slide sleeve sits between the abutment and the inner wall of the impression cap resting on the implant shoulder. For transferring the impression obtained from the original situation to a master cast, prefabricated parts analogous to this original situation are provided.

The implant shoulder is embodied by a manipulation shoulder sleeve with an upper manipulation shoulder and with a holding mechanism, possibly in the form of a locking edge, and the manipulation shoulder is gripped by the snap element of the impression cap. For transferring the impression obtained from the original situation to a master cast, an abutment of a manipulation implant is provided which can be pushed into the impression cap and slide sleeve remaining in the impression obtained. In terms of its outer contour, this push-in abutment is identical in shape to the abutment actually used in the original situation.

Underneath the abutment, the manipulation implant is advantageously provided with a continuation having retention plates and a fixing member complementing the holding mechanism, the holding mechanism of the manipulation shoulder sleeve cooperating with the fixing member of the manipulation implant.

By virtue of the invention, an impression system with an impression cap is now available by means of which taking an impression of an implant end protruding from the tissue structure of a patient, with a possible superstructure, and the production of a master cast are greatly simplified. In addition, the transfer of the actual geometrical situation on the patient to the master cast is now more precise.

BRIEF DESCRIPTION OF THE ATTACHED DRAWINGS

FIG. 5B: the view according to FIG. 5A with slide sleeve pushed on;

FIG. 5C: the view according to FIG. 5B with impression cap pushed on;

FIG. 6B: the view according to FIG. 6A with impression cylinder screwed on;

FIG. 6C: the view according to FIG. 6B with laterally open impression cap pushed on;

ILLUSTRATIVE EMBODIMENTS

A detailed description of illustrative embodiments of the impression system according to the invention is given hereinbelow with reference to the attached drawings, and possible modifications are discussed by way of conclusion.

The following statement applies to the whole of the description. If, for the purposes of clarity of the drawings, reference numbers are included in a figure but are not mentioned in the directly associated text of the description, then reference is made to their mention in preceding figure descriptions. In the interests of intelligibility, the repeated designation of components in succeeding figures is for the most part omitted, if it is clear from the drawings that the components concerned are "recurring" components.

FIGS. 1A to 1G

Without wishing to limit the invention thereto, the example further refers to the taking of an impression of an implant 1 fitted in the mouth of a patient, here a dental implant as a full screw. The implant 1 has an implant head 10 widening conically upwards, and an implant shoulder 11 narrowing conically upwards. A superstructure part, here a solid conical superstructure 2, is screwed into the implant 1 via its threaded part 20 into the internal threaded bore 12 of the implant 1. The abutment 21 of the solid conical superstructure 2 projecting above the implant shoulder 11 has several vertically extending grooves 22 on the outside. Thus far, the parts are known per se.

For taking an impression, use is made of a slide sleeve 3 which is divided into a sleeve section 30 open at the bottom, and a closed end-piece 31 which ends at the top. The cylindrical sleeve section 30 is smooth on the outside, while it has an inner contour 32 complementing the abutment 21 and can be pushed onto this abutment 21.

The impression cap 4 is in principle cylindrical and open at both ends. The channel passage 40 running through the impression cap 4 is complementary to the outer shape of the sleeve section 30, so that the impression cap 4 can be pushed in a sliding movement over the slide sleeve 3. At the very bottom, the impression cap 4 has a cap shoulder 41 which is complementary to the implant shoulder 11. On the outside, the cap shoulder 41 is surrounded by an elastic snap element 42 directed inwards so that it can snap over the implant shoulder 11 and releasably grip an undercut contour 13 on the implant head 10 (see FIGS. 1E and 1G). On the outer circumference, the impression cap 4 is radially grooved, so that several retention plates 43 are obtained. Apertures 44 may be present in the impression cap 4 for the escape of air and for the penetration or introduction of impression compound. The retention plates 43 have the function of anchoring in the impression compound, in order to prevent the displacement or twisting of the impression cap 4.

In the assembled state, the slide sleeve 3 pushed onto the abutment 21 reaches via the sleeve section 30 almost as far as the implant shoulder 11. The impression cap 4 receives the sleeve section 30 in its channel passage 40, with the end-piece 31 projecting upwards from the impression cap 4. The inner contour 32 of the slide sleeve 3 bears snugly on the outer contour of the abutment 21. In particular, the lower edge of the sleeve section 30 acts as a clamping wedge between the abutment 21 and the impression cap 4. The cap shoulder 41 sits practically seamlessly on the implant shoulder 11 and with resilient tensioning, the snap element 42 gripping over the implant shoulder 11 in a downward direction, towards the implant head 10, and as it were pulling the impression cap 4 onto the implant 1.

FIGS. 2A to 2E

This sequence of figures refers to the production of the master cast after the impression of the mouth situation has been obtained. The above-described slide sleeve 3 and impression cap 4, which remain embedded in the impression, are present once again. A manipulation implant 5, here with a solid conical abutment 51, and a manipulation shoulder sleeve 6 are added in this work phase.

The manipulation implant 5 has, at the bottom, a continuation 50 and, at the top, an abutment 51 identical to the abutment 21. Above the continuation 50 with a plurality of retention plates 52, the manipulation implant 5 has a fixing plate 53 with a plate shoulder 54.

Figure 1A:
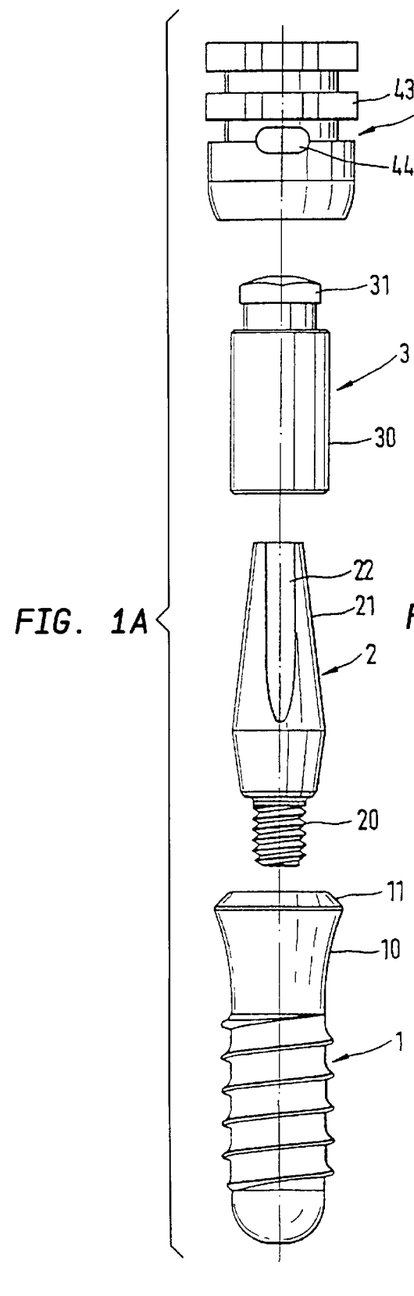
FIG. 1A: a full screw implant with a solid conical superstructure, a slide sleeve and the impression cap in an exploded view.
Figure 1B:
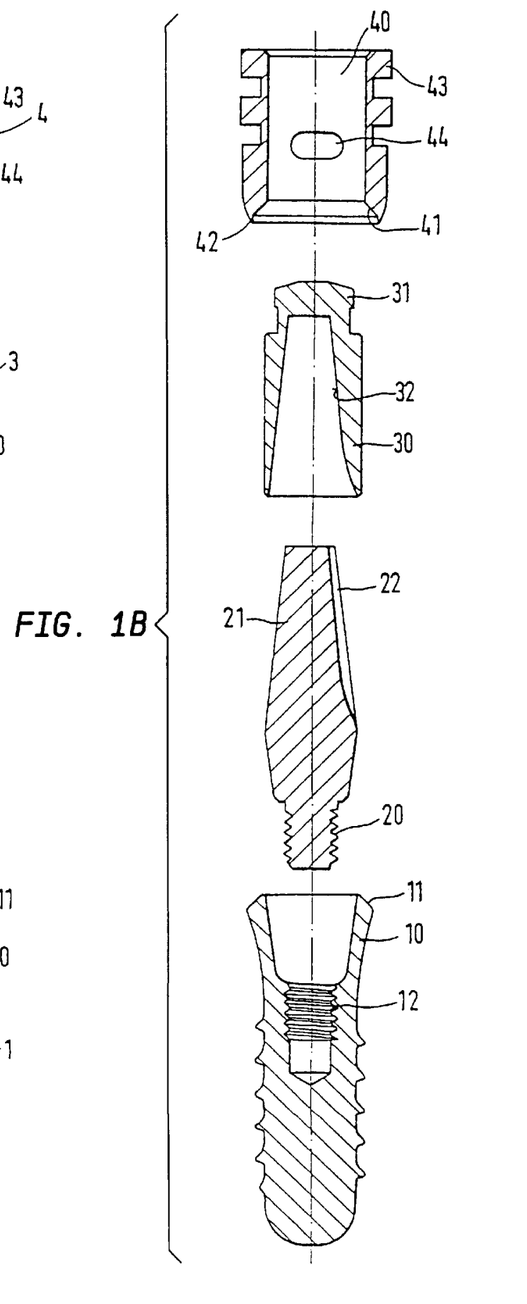
FIG. 1B: the view according to FIG. 1A in vertical section.
Figure 1C:
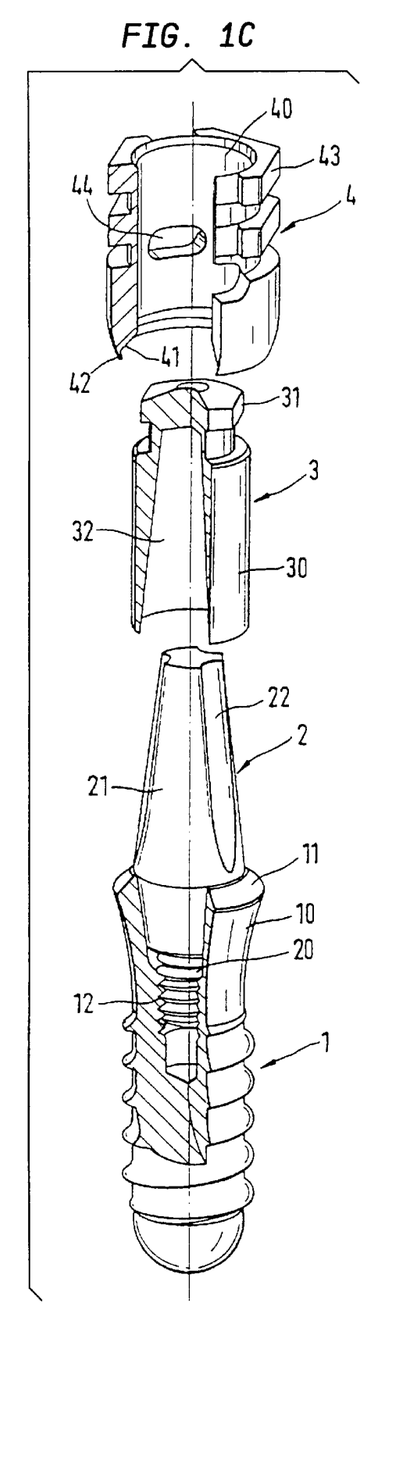
FIG. 1C: the view according to FIG. 1A with screwed-in solid conical superstructure in partial section.
Figure 1D:
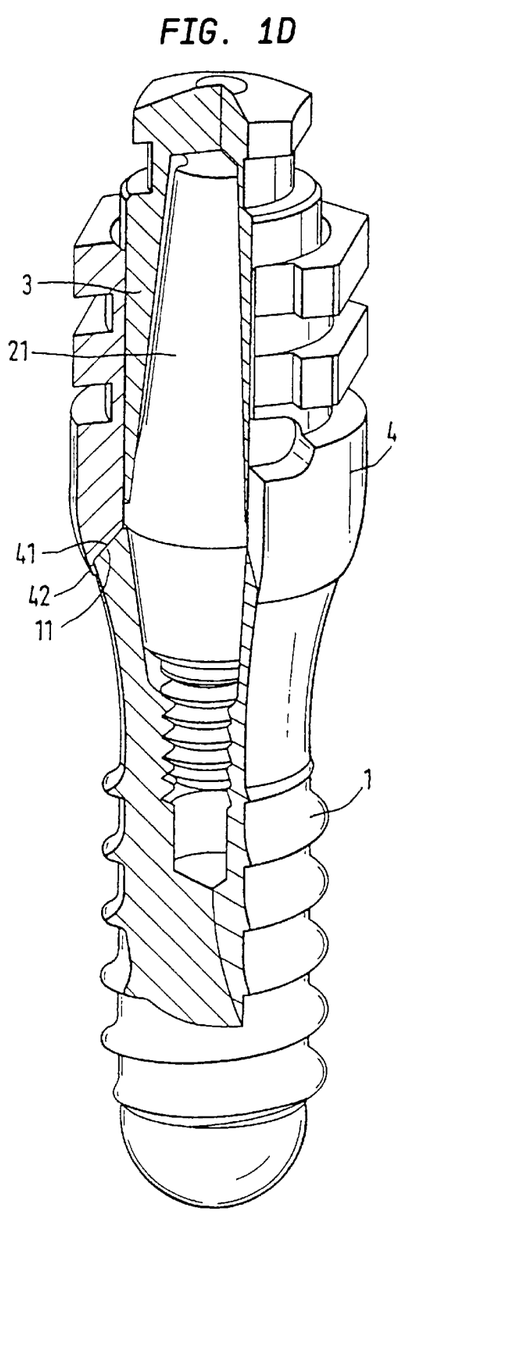
FIG. 1D: the elements according to FIG. 1A in the assembled state, as partial section.
Figure 1E:
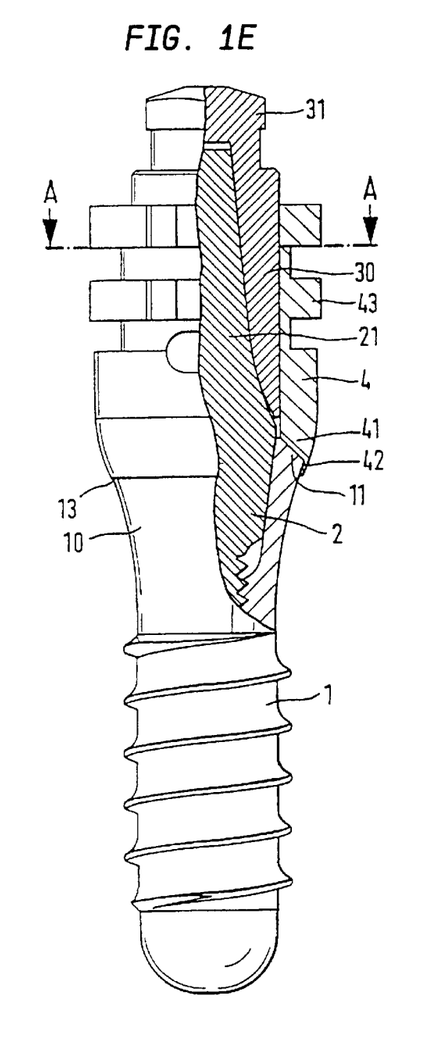
FIG. 1E: the view according to FIG. 1D in another partial section.
Figure 1F:
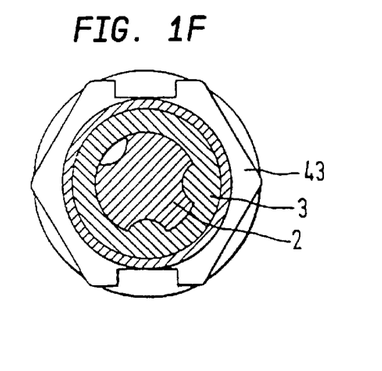
FIG. 1F: the view according to FIG. 1E as section along the line A—A.
Figure 1G:
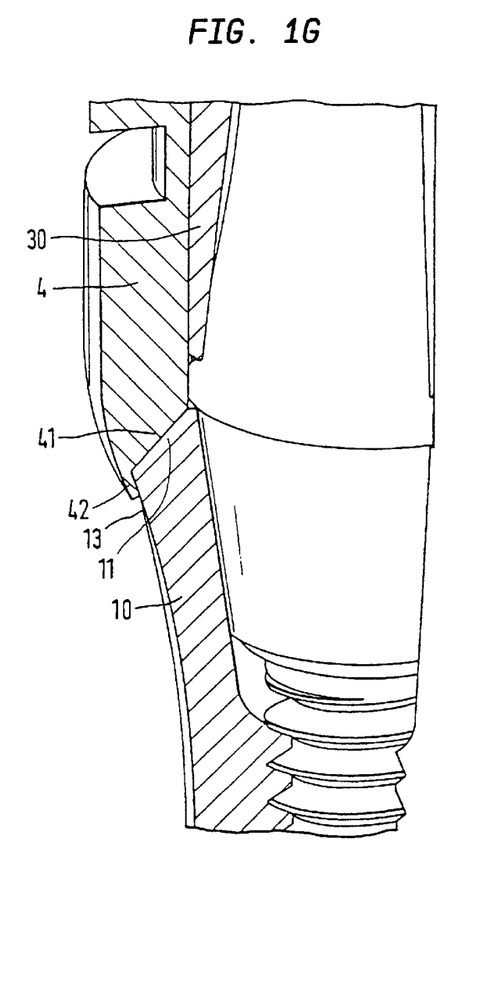
FIG. 1G: as detail, the area with the snap element engaging around the implant shoulder, in partial section.
Figure 2A:
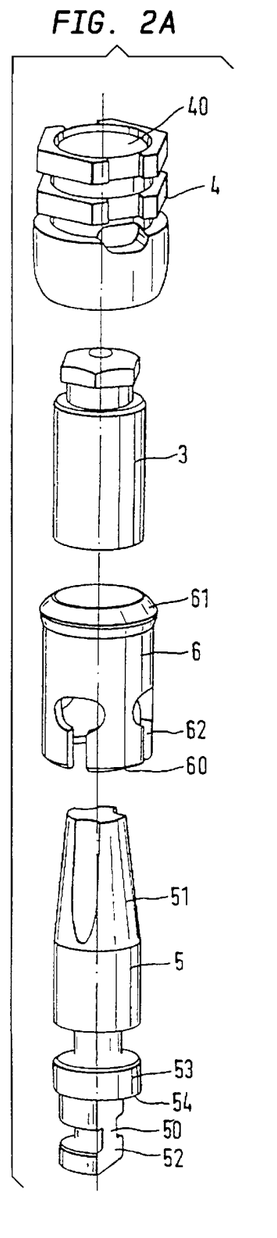
FIG. 2A: a manipulation implant with solid conical part, a manipulation shoulder sleeve, a slide sleeve and the impression cap in an exploded view.
Figure 2B:
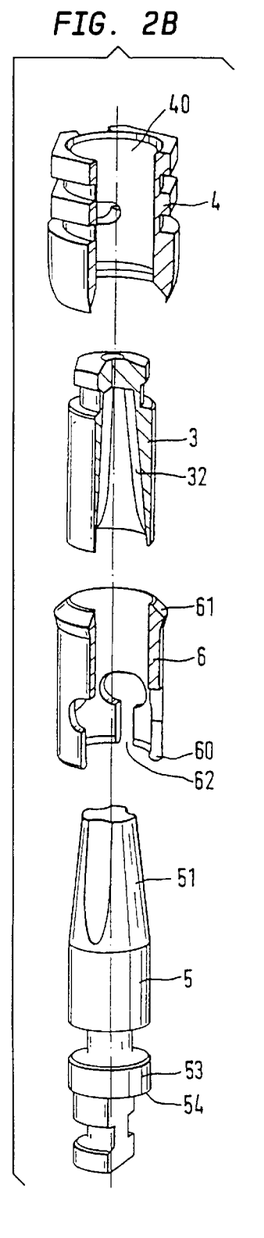
FIG. 2B: the view according to FIG. 2A in vertical partial section.
Figure 2C:
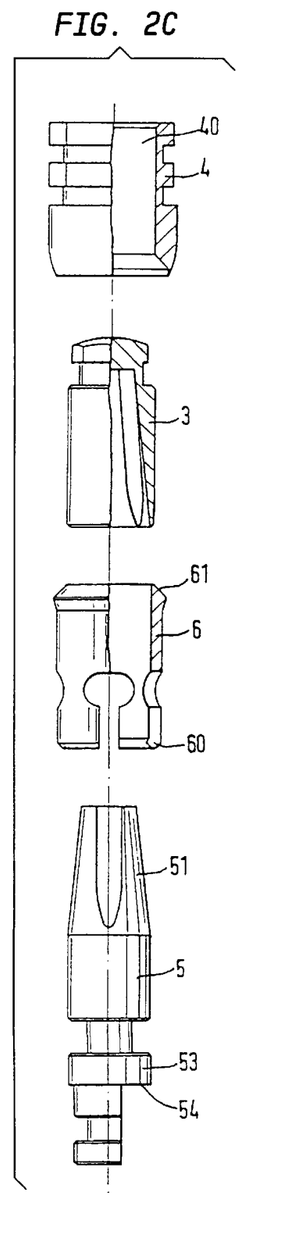
FIG. 2C: the view according to FIG. 2B in another vertical partial section.
Figure 2D:
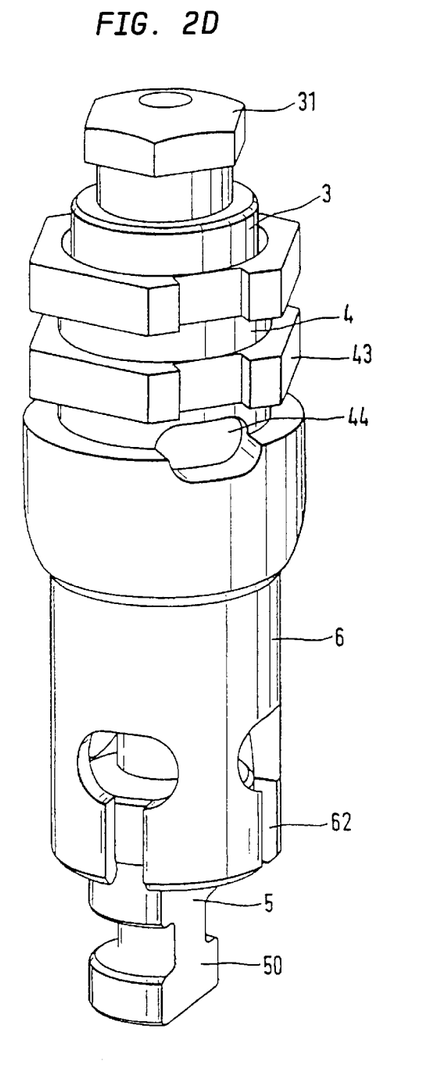
FIG. 2D: the elements according to FIG. 2A in the assembled state.
Figure 2E:
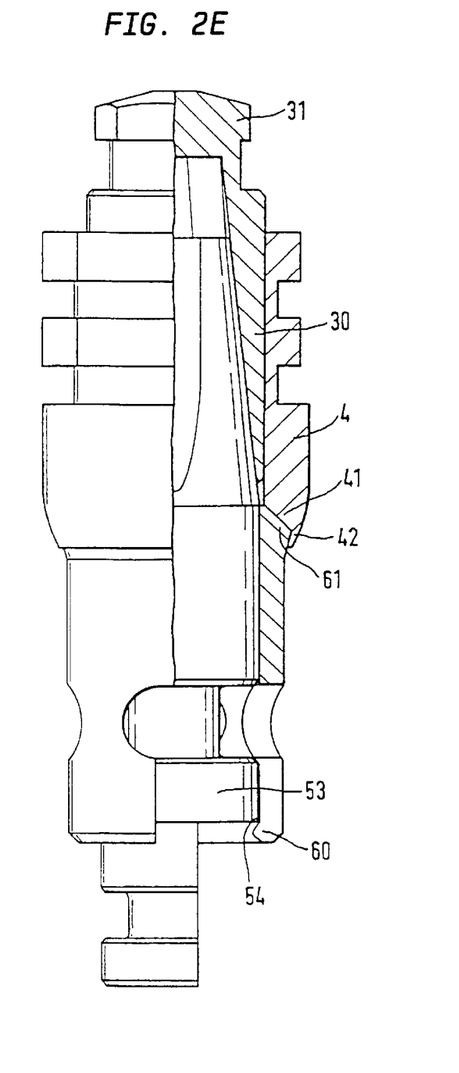
FIG. 2E: the view according to FIG. 2D in vertical partial section.
Figure 3A:
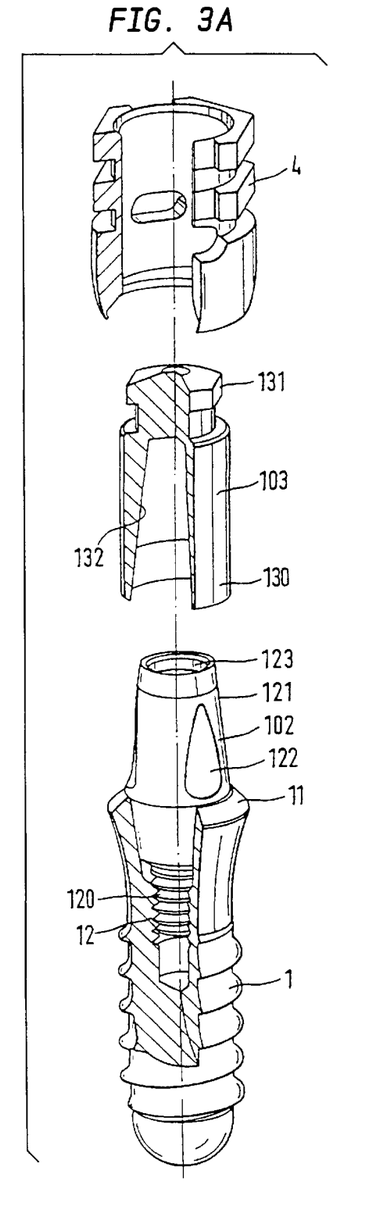
FIG. 3A: a full screw implant with a conical superstructure (6°) with internal thread, a slide sleeve and the impression cap in an exploded view.
Figure 3B:
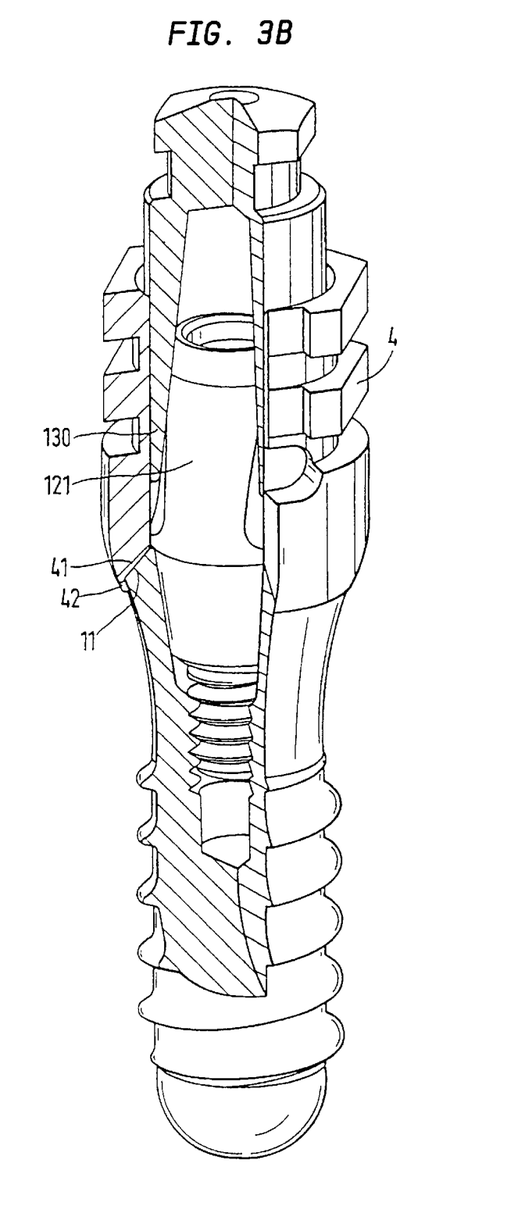
FIG. 3B: the elements according to FIG. 3A in the assembled state, in vertical partial section.

The cylindrical, hollow manipulation shoulder sleeve 6 has, at the bottom, a radially encircling, elastic locking edge 60 curved inwards. At the top, the manipulation shoulder sleeve 6 terminates via a manipulation shoulder 61 identical to the implant shoulder 11. In the manipulation shoulder sleeve 6 there are expansion slots 62 extending to the locking edge 60 for the purpose of increasing the elasticity. In the assembled state, the manipulation shoulder sleeve 6 is pushed so far onto the manipulation implant 5 that the locking edge 60 engages around the fixing plate 53, while the snap element 42 of the impression cap 4 engages elastically around the manipulation shoulder 61. The slide sleeve 3 again clamps wedge-like in the impression cap 4.
FIGS. 3A and 3B

In a modification to the sequence of FIGS. 1A to 1G, instead of the solid conical superstructure 2, a conical superstructure 102 having an internal thread 123 is shown here. The threaded part 120 engages in the internal threaded bore 12 of the implant 1. The conical abutment 121 with the grooves 122 and, for example, a conicity of 6° has another outer geometry; an adapted slide sleeve 103 with an inner contour 132 complementary to the abutment 121 is accordingly provided. At the very bottom, the sleeve section 130 has an inner contour of 6° conicity; which then merges into an 8° conicity.

Figure 3C:
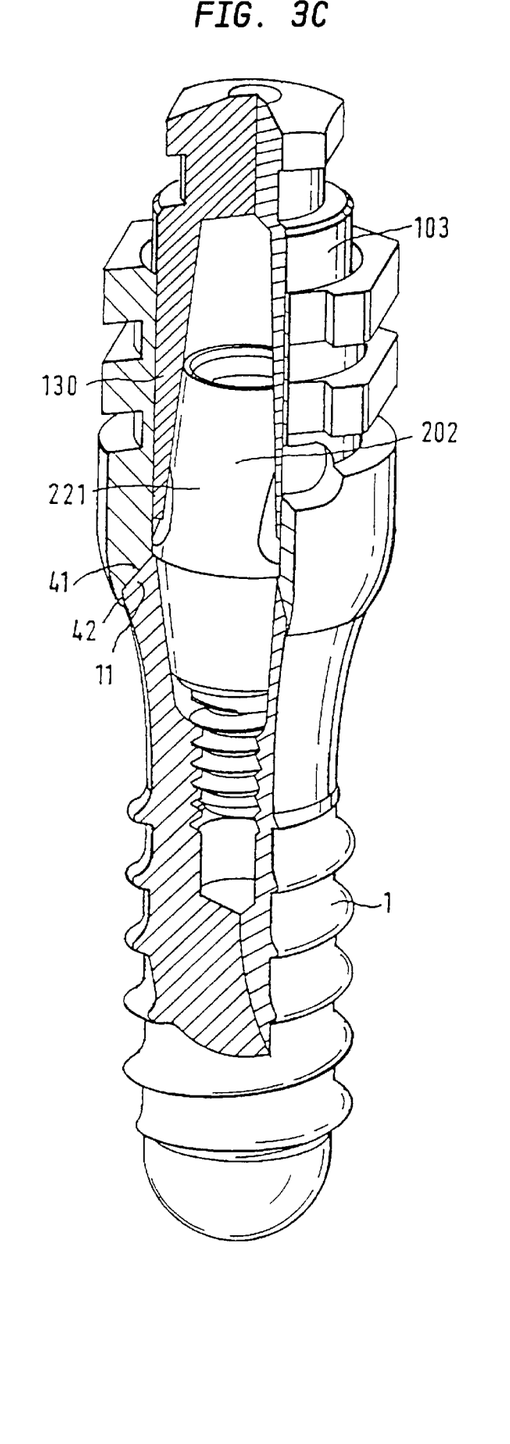
FIG. 3C: the view according to FIG. 3B with a conical superstructure (8°)
Figure 4A:
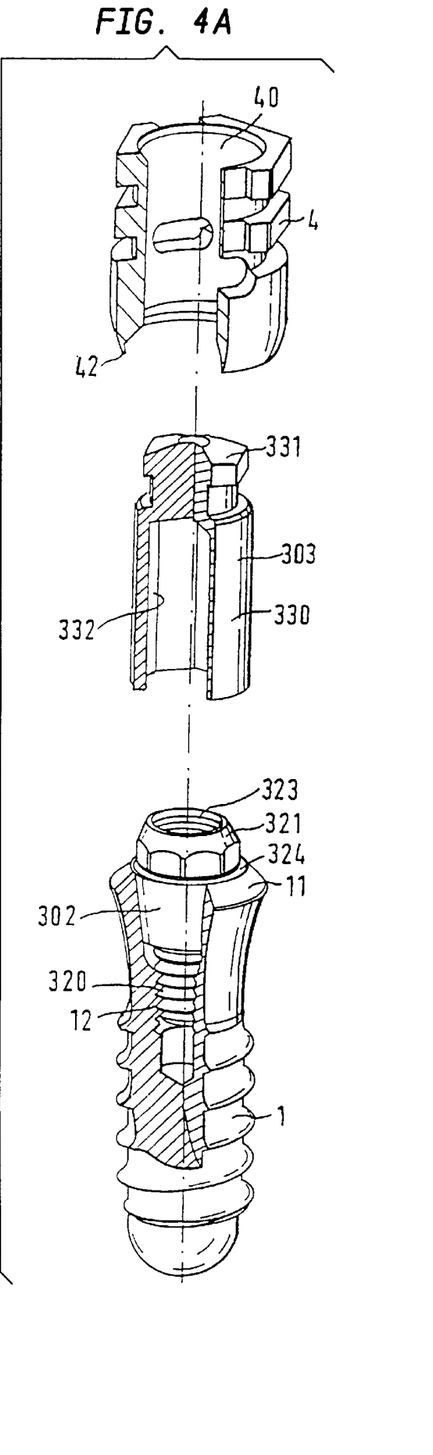
FIG. 4A: a full screw implant with a polygonal superstructure, a slide sleeve and the impression cap as an exploded view in vertical partial section.
Figure 4B:
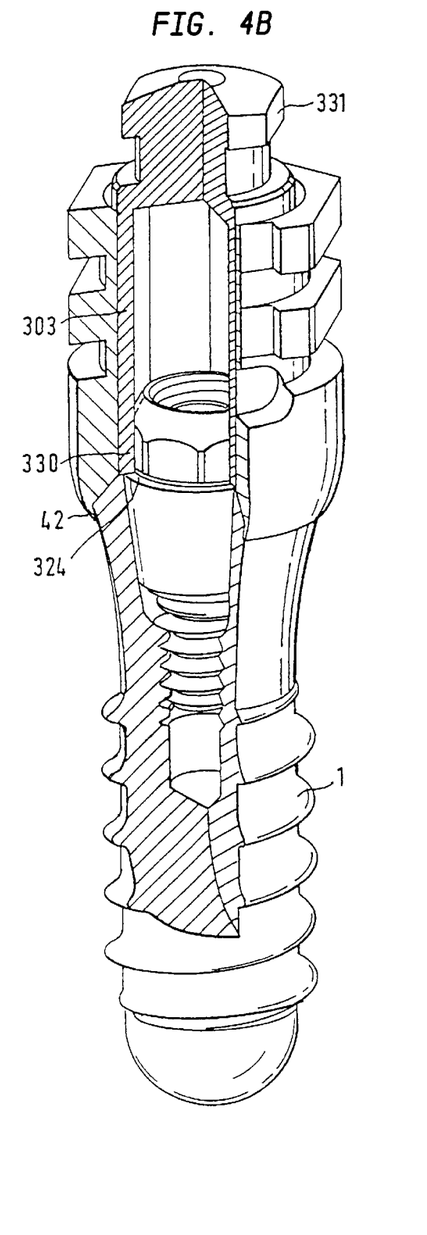
FIG. 4B: the elements according to FIG. 4A in the assembled state, in vertical partial section.
Figure 4C:
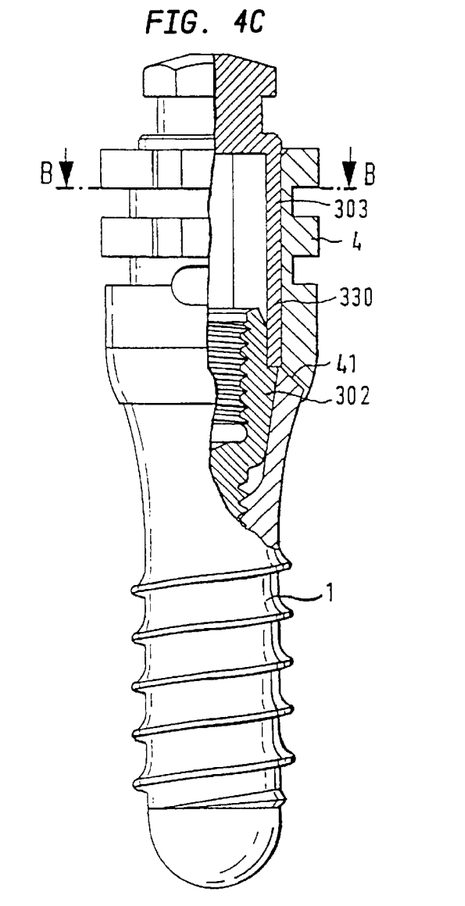
FIG. 4C: the view according to FIG. 4B in another vertical partial section.
Figure 4D:
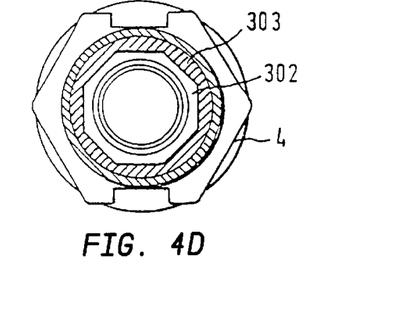
FIG. 4D: the view according to FIG. 4C as section along the line B—B.

In the assembled state the snap element 42 again engages around the implant shoulder 11, and the lower edge of the sleeve section 130 pushes and clamps itself in the manner of a wedge between the abutment 121 and the impression cap 4. The end-piece 131 of the slide sleeve 103 projects upwards from the impression cap 4. The manipulation implant to be used here would have to have an abutment identical to the abutment 121.
FIG. 3C

A once again modified conical superstructure 202 is used; it has, for example, a conicity of 8° on the abutment 221. With the two stepped conicities of 6° and 8° in the sleeve section 130, the slide sleeve 103 can also be used here.
FIGS. 4A to 4D

A polygonal superstructure 302 is now screwed with its threaded part 320 into the internal threaded bore 12 of the implant 1. The polygonal abutment 321, here with an outer octagon, projects above the implant shoulder 11, while the horizontal abutment shoulder 324 radially surrounding the abutment 321 ends approximately flush, depending on tolerances, with the top edge of the implant shoulder 11. An internal threaded bore 323 in the form of a blind hole extends axially into the polygonal superstructure 302. A slide sleeve 303 is provided with an inner contour 332 matching the abutment 321 on the sleeve section 330.

In the assembled state, the lower edge of the sleeve section 330 sits on the abutment shoulder 324 and the end-piece 331 again projects from the impression cap 4 at the top. The snap element 42 of the impression cap 4 engages around the implant shoulder 11.
FIGS. 5A to 5H

Figure 5A:
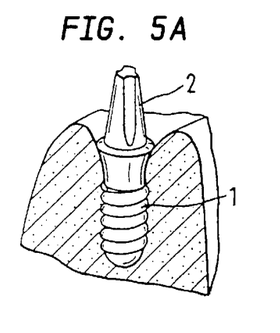
FIG. 5A: mouth situation with full screw implant sitting in the jaw bone, and solid conical superstructure fitted.
Figure 5B:
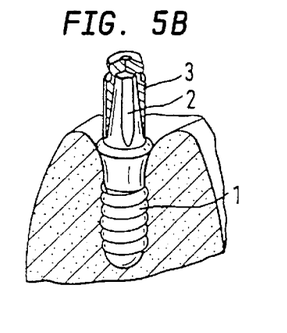
Figure 5C:
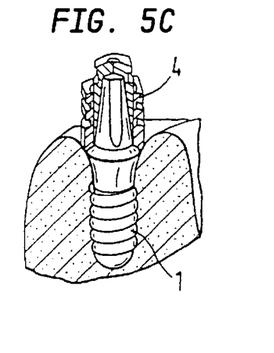
Figure 5D:
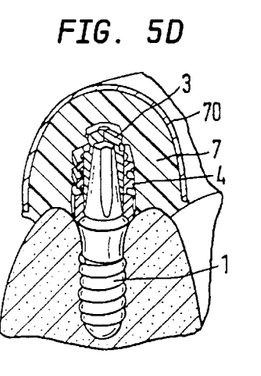
FIG. 5D: the view according to FIG. 5C with impression tray applied.
Figure 5E:
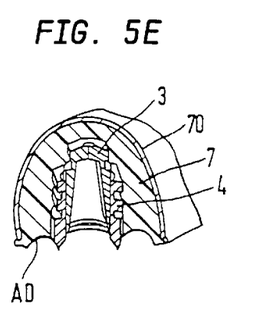
FIG. 5E: the impression obtained according to FIG. 5D.

This sequence of figures outlines the work steps involved from the impression-taking, using the example of a solid conical superstructure 2, to the finished master cast. The mouth situation (FIG. 5A) is shown with an implant 1 sitting in the jaw bone and a solid conical superstructure 2 screwed into the implant 1. In order to take an impression, the slide sleeve 3 is first of all pushed onto the solid conical superstructure 2 (FIG. 5B). In a further step, the impression cap 4 is pushed on (FIG. 5C). The sequence of pushing on the slide sleeve 3 and the impression cap 4 could also take place in the reverse order. The impression tray 70 filled with impression compound 7 is now pressed onto the implant 1 thus equipped in the direction of the jaw bone (FIG. 5D). After withdrawing the impression tray 70, the impression cap 4 and the slide sleeve 3 remain embedded in the impression compound 7, and the impression AD is obtained (FIG. 5E).

Figure 5F:
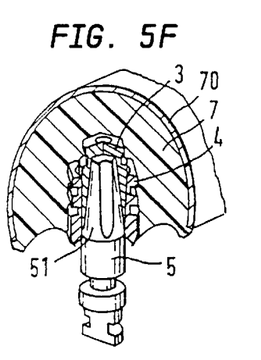
FIG. 5F: the solid conical superstructure applied on the impression according to FIG. 5E.
Figure 5G:
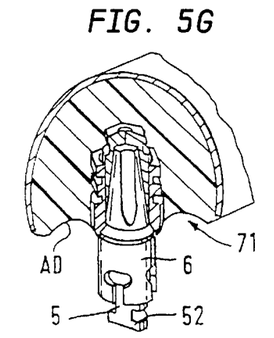
FIG. 5G: the view according to FIG. 5F with manipulation shoulder sleeve attached.
Figure 5H:
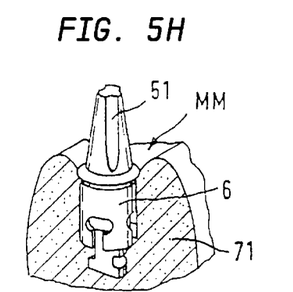
FIG. 5H: the view according to FIG. 5G with impression tray removed.

An analogous manipulation implant 5 is now pushed via its conical abutment 51 into the slide sleeve 3 as far as the limit stop (FIG. 5F). Finally, the manipulation shoulder sleeve 6 is pushed over the retention plates 52 of the manipulation implant 5 until its manipulation shoulder 61 is held by the snap element 42, with the locking edge 60 striking the plate shoulder 54 (FIG. 5G). Modelling compound 71 is lastly poured onto the impression AD and the master cast MM is obtained (FIG. 5H). It is also conceivable to insert the manipulation shoulder sleeve 6 before the manipulation implant 5.
FIGS. 6A to 6H

Figure 6A:
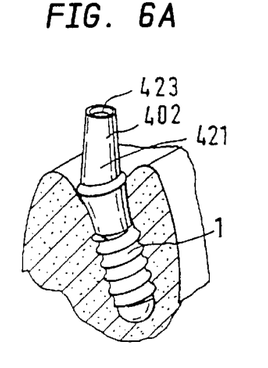
FIG. 6A: the view according to FIG. 5A with angled conical superstructure.
Figure 6B:
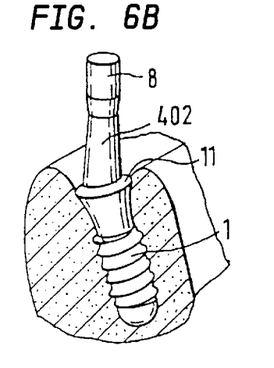
Figure 6C:
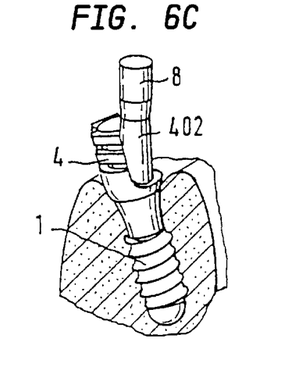
Figures 6D, 6E:
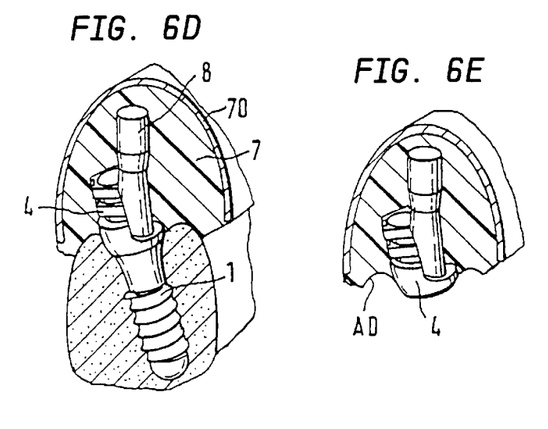
FIG. 6D: the view according to FIG. 6C with impression tray applied.
FIG. 6E: the impression according to FIG. 6D.
Figure 6F:
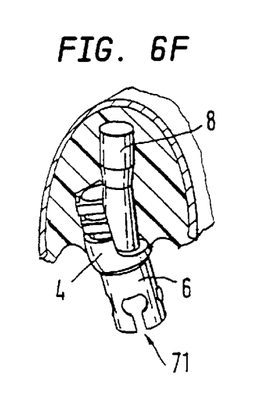
FIG. 6F: the view according to FIG. 6E with manipulation shoulder sleeve attached.
Figure 6G:
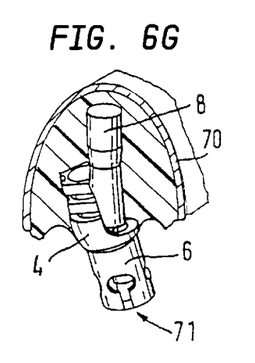
FIG. 6G: the view according to FIG. 6F with filled impression cap.
Figure 6H:
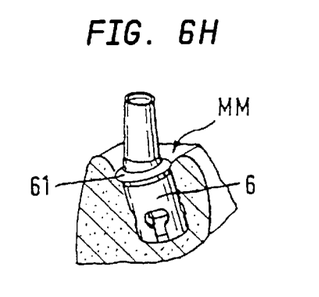
FIG. 6H: the view according to FIG. 6G as finished master cast.

This sequence of figures outlines the work steps taking the example of an angled conical superstructure 402 with an internal thread 423, where the threaded part 420 is screwed into the internal threaded bore 12 in the implant 1; this is the mouth situation (FIG. 6A). An impression cylinder 8 is screwed into the internal thread 423 (FIG. 6B) and a laterally open impression cap 4 is pushed onto the latter and grabs the implant shoulder 11 (FIG. 6C). The impression AD is taken using the impression tray 70 filled with impression compound 7 (FIG. 6D), which impression is obtained after withdrawing the impression tray 70, and in which the impression cap 4 and a hollow space according to the impression cylinder 8 and the conical superstructure 402 remain behind (FIG. 6E). In the next step, the impression cylinder 8 is pushed into its hollow space and the manipulation shoulder sleeve 6 is attached (FIG. 6F) and modelling compound 71 is then filled in through the manipulation shoulder sleeve 6, so that the whole hollow space is filled up (FIG. 6G). Modelling compound 71 is now poured onto the impression AD and, after removing the impression tray 70 in which the impression cylinder 8 remains, the finished master cast MM is obtained (FIG. 6H).

Further constructional variations can be made to the impression system described above. The following are mentioned expressly here:

- The slide sleeve 3 can be omitted entirely if the hollow space remaining in the impression cap 4, and left by the selected abutment, e.g. 21, inside the impression cap 4, is filled with impression compound. The impression compound could be introduced through the apertures 44.
- From the point of view of production engineering, it may be advantageous for the slide sleeve 3 and the impression cap 4 to be combined and designed as one piece.
- It is feasible for the manipulation implant 5 and the manipulation shoulder sleeve 6 to be combined and designed as one piece.
- The list of abutments 21, 131, 221, 321, 421 set out hitherto in the description is not by any means exhaustive. Other abutment forms besides these ones are also considered to be included.

Like the impression cap 4, the manipulation shoulder sleeve 6 can have, on the outer circumference, retention plates generated by radial grooving and/or radially directed apertures.

The manipulation implant 5 and/or the manipulation shoulder sleeve 6 can be omitted entirely if the hollow space remaining in the impression AD is filled with modelling material.

The inventive concept can be generalized to the extent that the snap elements 42 provided on the impression cap 4 can generally have an engagement geometry engaging in the undercut contour present on the outer side of the implant end directed outwards. The contour can be created by a trumpet shape of the implant end or by an incorporated undercut.

What is claimed is:

1. An impression cap for a dental impression system, comprising:

a sleeve-shaped body having a first end and a second end, at least said second end being provided with an opening;

said opening extending longitudinally into said body from said second end;

gripping means, extending from said second end of said body, for gripping an undercut contour of a dental implant; and an inner circumferential shoulder located at said second end of said body and having a size and shape complementary to an outer circumferential shoulder of a dental implant gripped by said gripping means.

2. An impression cap according to claim 1, wherein said gripping means includes a circular lip which extends completely around said second end of said body.

3. An impression cap according to claim 2, wherein said lip is elastic and is directed radially inwardly toward said opening of said impression cap, whereby said lip snaps over an outer circumferential shoulder of a dental implant gripped by said gripping means.

4. An impression cap according to claim 1, wherein said body includes a cylindrical side wall having an outer surface; and at least one retention plate extending radially outwardly from said outer surface of said body.

5. An impression cap according to claim 1, wherein said body includes a cylindrical side wall; and at least one aperture located in said side wall between said first end and said second end of said body.

6. An impression cap according to claim 1, wherein said gripping means includes a plurality of gripping lips which extend around said second end of said body.

7. An impression cap according to claim 6, wherein said lips are elastic and are directed radially inwardly toward said opening of said impression cap, whereby said lips snap over an outer circumferential shoulder of a dental implant gripped by said gripping means.

8. An impression system, comprising:

an implant, including an implant head, an implant shoulder located above said implant head, an undercut contour, and an internal threaded bore;

a superstructure, including a retention part at one end thereof and an abutment head positioned adjacent to said retention part, said retention part being fixed in said internal threaded bore of said implant;

an impression cap positioned on said implant shoulder, said impression cap including a sleeve-shaped body having a first end and a second end, at least said second end being provided with an opening, said opening extending longitudinally into said body from said second end, and gripping means, extending from said second end of said body, for gripping said undercut contour of said dental implant; and a slide sleeve positioned on said abutment head between said abutment head and said impression cap.

9. An impression system according to claim 8, wherein said slide sleeve includes a cylindrical sleeve section having one end which is open and an inner contour complementary to said abutment head; and a closed end piece positioned adjacent to said cylindrical sleeve section, such that said slide sleeve is open only at said one end of said cylindrical sleeve section, said closed end piece having retention elements.

10. An impression system according to claim 8, wherein said gripping means includes a circular lip which extends completely around said second end of said body.

11. An impression system according to claim 10, wherein said lip is elastic and is directed radially inwardly toward said opening of said impression cap, whereby said lip snaps over said implant shoulder.

12. An impression system according to claim 8, wherein said impression cap further includes an inner circumferential shoulder located at said second end of said body, said inner circumferential shoulder having a size and shape complementary to said implant shoulder.

13. An impression system according to claim 8, wherein said body of said impression cap includes a cylindrical side wall having an outer surface; and at least one retention plate extending radially outwardly from said outer surface of said body.

14. An impression system according to claim 8, wherein said body of said impression cap includes a cylindrical side wall; and at least one aperture located in said side wall between said first end and said second end of said body.

15. An impression system according to claim 8, further comprising a manipulation implant, including a manipulation abutment head which is identical to said abutment head of said superstructure; and a manipulation shoulder sleeve including an upper end and a lower end, a manipulation shoulder located at said upper end, said manipulation shoulder being sized and shaped analogously to said implant shoulder and having an undercut, such that said gripping means of said impression cap grips said undercut of said manipulation shoulder, and holding means, located at said lower end, for holding said manipulation shoulder sleeve on said manipulation implant.

16. An impression system according to claim 15, wherein said holding means includes an inwardly curving elastic locking edge which encircles said lower end of said manipulation shoulder sleeve.

17. An impression system according to claim 15, wherein said manipulation shoulder sleeve includes a plurality of expansion slots in said lower end such that said lower end is expandable.

18. An impression system according to claim 15, wherein said manipulation implant includes a fixing plate located below said manipulation abutment head, said holding means of said manipulation shoulder sleeve fitting around said fixing plate; and a continuation extending below said fixing plate, said continuation including a plurality of retention elements.

19. An impression system according to claim 8, wherein said gripping means includes a plurality of gripping lips which extend around said second end of said body.

20. An impression system according to claim 19, wherein said lips are elastic and are directed radially inwardly toward said opening of said impression cap, whereby said lips snap over said implant shoulder.

21. In combination, a dental implant having an undercut contour and means for receiving an abutment; and an impression cap having a sleeve-shaped body including a first end and a second end, at least said second end being provided with an opening, and gripping means extending from said second end of said body and releasably gripping said undercut contour of said dental implant.

22. A combination according to claim 21, wherein said gripping means includes a circular lip which extends completely around said second end of said body.

23. A combination according to claim 22, wherein said dental implant includes an outer circumferential shoulder and said lip is elastic and is directed radially inwardly toward said opening of said impression cap, whereby said lip snaps over said outer circumferential shoulder of said dental implant.

24. A combination according to claim 21, wherein said impression cap includes an inner circumferential shoulder located at said second end of said body and having a size and shape complementary to said outer circumferential shoulder of said dental implant.

25. A combination according to claim 21, wherein said body includes
   a cylindrical side wall having an outer surface; and
   at least one retention plate extending radially outwardly from said outer surface of said body.

26. A combination according to claim 21, wherein said body includes
   a cylindrical side wall; and
   at least one aperture located in said side wall between said first end and said second end of said body.

27. A combination according to claim 21, wherein said gripping means includes a plurality of gripping lips which extend around said second end of said body.

28. A combination according to claim 27, wherein said lips are elastic and are directed radially inwardly toward said opening of said impression cap, whereby said lips snap over said outer circumferential shoulder of said dental implant.

29. An impression cap for a dental impression system, comprising:
   a cylindrical body having a first end and a second end, said first and second ends being open, a cylindrical side wall, and at least one aperture located in said side wall between said first end and said second end;
   a passage extending longitudinally through said body from said first end to said second end; and
   gripping means, extending from said second end of said body, for gripping over an outer circumferential shoulder of a dental implant gripped by said gripping means.

30. An impression cap according to claim 29, wherein said gripping means includes a circular lip which extends completely around said second end of said body.

31. An impression cap according to claim 30, wherein said lip is elastic and is directed radially inwardly toward said passage of said impression cap, whereby said lip snaps over an outer circumferential shoulder of a dental implant gripped by said gripping means.

32. An impression cap according to claim 29, wherein said gripping means includes a plurality of gripping lips which extend around said second end of said body.

33. An impression cap according to claim 2, wherein said lips are elastic and are directed radially inwardly toward said passage of said impression cap, whereby said lips snap over an outer circumferential shoulder of a dental implant gripped by said gripping means.

34. An impression cap according to claim 29, further comprising an inner circumferential shoulder located at said second end of said body and having a size and shape complementary to an outer circumferential shoulder of a dental implant gripped by said gripping means.

35. An impression cap according to claim 29, wherein said body includes
   a cylindrical side wall having an outer surface; and
   at least one retention plate extending radially outwardly from said outer surface of said body.

36. In combination, a dental implant having an outer circumferential shoulder; and an impression cap having a cylindrical body including a first end and a second end, said first and second ends being open, a cylindrical side wall, at least one aperture located in said side wall between said first and second ends, a passage extending longitudinally through said body from said first end to said second end, and gripping means, extending from said second end of said body, for gripping over said outer circumferential shoulder of said dental implant.

37. A combination according to claim 36, wherein said gripping means includes a circular lip which extends completely around said second end of said body.

38. A combination according to claim 37, wherein said lip is elastic and is directed radially inwardly toward said passage of said impression cap, whereby said lip snaps over said outer circumferential shoulder.

39. A combination according to claim 36, wherein said gripping means includes a plurality of gripping lips which extend around said second end of said body.

40. A combination according to claim 39, wherein said lips are elastic and are directed radially inwardly toward said passage of said impression cap, whereby said lips snap over an outer circumferential shoulder of said dental implant.

41. A combination according to claim 36, wherein said impression cap includes an inner circumferential shoulder located at said second end of said body and having a size and shape complementary to said outer circumferential shoulder of said dental implant.

42. A combination according to claim 36, wherein said body includes
   a cylindrical side wall having an outer surface; and
   at least one retention plate extending radially outwardly from said outer surface of said body.

* * * * *